United States Patent [19]

Morris et al.

[11] Patent Number: 4,581,381

[45] Date of Patent: Apr. 8, 1986

[54] SOFT HOMOGENEOUS ANTACID TABLET

[75] Inventors: William M. Morris, Rancho Palos Verdes, Calif.; Frank Witzel, Saratoga Springs, N.Y.; Wayne J. Puglia, Bayville, N.Y.; Donald A. M. Mackay, Pleasantville, N.Y.; K. Warren Clark, Brewster, N.Y.; K. J. Patanasinth, Stamford, Conn.

[73] Assignee: Nabisco Brands, Inc., Parsippany, N.J.

[21] Appl. No.: 712,825

[22] Filed: Mar. 18, 1985

Related U.S. Application Data

[60] Division of Ser. No. 551,383, Nov. 14, 1983, which is a continuation-in-part of Ser. No. 341,967, Jan. 22, 1982, abandoned, which is a continuation of Ser. No. 175,179, Aug. 4, 1980, abandoned.

[51] Int. Cl.$^4$ .................. A61K 9/20; A61K 33/08; A61K 33/10; A61K 33/12
[52] U.S. Cl. ................................. 514/819; 427/3; 424/154; 424/155; 424/156; 424/157
[58] Field of Search .................. 424/38, 154–157; 427/2, 3

[56] References Cited

U.S. PATENT DOCUMENTS

| | | | |
|---|---|---|---|
| 780,226 | 1/1905 | Pink | 424/38 |
| 1,546,820 | 7/1925 | Ballard | 424/38 |
| 1,851,165 | 3/1932 | Farr | 424/38 |
| 1,991,139 | 2/1935 | Clark | 424/38 |
| 2,461,399 | 2/1949 | Strausser | 424/38 |
| 2,682,471 | 6/1954 | Alther | 424/38 X |
| 2,926,121 | 2/1960 | Hobbs et al. | 424/156 |
| 2,955,548 | 10/1960 | Himmler | 424/38 X |
| 3,253,988 | 5/1966 | Scott | 424/156 |
| 3,456,050 | 7/1969 | Reickemann et al. | 424/38 |
| 3,536,074 | 10/1970 | Aufhauser | 424/38 X |
| 3,843,778 | 10/1974 | Diamond | 424/156 |
| 4,163,777 | 8/1979 | Mitra | 424/21 |
| 4,230,693 | 10/1980 | Izzo et al. | 424/156 |
| 4,271,142 | 6/1981 | Puglia et al. | 424/14 |
| 4,303,648 | 12/1981 | Witzel et al. | 424/158 |
| 4,327,076 | 4/1982 | Puglia et al. | 424/38 |
| 4,327,077 | 4/1982 | Puglia et al. | 424/38 |

FOREIGN PATENT DOCUMENTS

| | | | |
|---|---|---|---|
| 2056 | of 1855 | United Kingdom | 424/38 |
| 8869 | of 1888 | United Kingdom | 424/15 |
| 126894 | of 1907 | United Kingdom | 424/156 |
| 392 | of 1913 | United Kingdom | 424/156 |
| 471116 | 8/1937 | United Kingdom | 424/38 |
| 543309 | 2/1942 | United Kingdom | 424/38 |
| 1414121 | 11/1975 | United Kingdom | 424/157 |
| 1538280 | 1/1979 | United Kingdom | 424/156 |
| 2009597A | 6/1979 | United Kingdom | 424/156 |
| 2030042A | 4/1980 | United Kingdom | 424/157 |
| 140168 | 6/1960 | U.S.S.R. | 424/38 |

OTHER PUBLICATIONS

Richmond Choice Confections Manufacturing Methods and Formulas, Manufacturing Confectioner Pub. Co., Oak Park, Ill. (1954), pp. 97–100, 103–104.
USPTO Translation of Seidenstricker, German Patent 832932 (1/31/62), Process for Making Chocolate Capsules for Filling with Medicaments.
Riegel, Chemical Process Machinery, 2nd Ed. (1953), Reinhold Publishing Corp., New York, N.Y., Chap. II, p. 286, Table 49, Classification of Mixing Devices–"Muller or Pan Mixer", FIGS. 246 & Text, Pan Mixers, FIG. 248; or Mullers.

*Primary Examiner*—Shep K. Rose
*Attorney, Agent, or Firm*—Richard Kornutik

[57] ABSTRACT

An improved deposited chewable antacid tablet containing solid antacid particles which includes solid antacid particles having a primary particle size of less than 100 millimicrons, which particles are thoroughly coated with a mixture composed of a fatty material or oil, a surfactant, and a flavorant selected from the group consisting of chocolate, mint-chocolate, butter, vanilla, butter fat and mint flavors. The fat or oil is present in an amount of from about 25% to about 45% of the mixture. As a result of the mixture coated on the antacid particles a non-chalky, non-gritty, antacid tablet is provided which readily disintegrates upon exposure to saliva as such way as to function as a liquid antacid.

11 Claims, No Drawings

SOFT HOMOGENEOUS ANTACID TABLET

Cross References to Related Patent Applications

This is a divisional of copending application Ser. No. 551,383, filed on Nov. 14, 1983, which is a continuation-in-part of application Ser. No. 341,967, filed Jan. 22, 1982, which is a continuation application Ser. No. 175,179, filed Aug. 4, 1980, said application Ser. No. 341,967 and Ser. No. 175,179 being now abandoned.

This application contains subject matter related to, but distinctly different from, the subject matter of U.S. Pat. No. 4,271,142 to Puglia, et al. and U.S. Pat. No. 4,303,648 to Witzel, et al.

BACKGROUND OF THE INVENTION

The present invention relates to the art of deposited antacid tablets and in particular, to a non-chalky flavored solid antacid tablet which disintegrates in the mouth to a smooth creamy pleasant-tasting emulsion devoid of the grittiness normally associated with antacids and which affords maximum surface contact of particles of the antacid.

Antacids generally available are of the insoluble type which function by raising the pH of the stomach to a desired value, between 4 and 5, and maintaining this pH for some period.

Insoluble antacids depend on surface area (antacid particle size) for their efficiency. The smaller the particle size, the larger the surface area—thus more contact between acid to be neutralized and the antacid neutralizer. Very small solid antacid particle size can be attained by operations such as milling. However, a chewable tabletted product requires the user to mascerate the tabletted mass with his teeth, an operation which does not provide the small particle size and increased surface area originally achieved in the milled antacid powder.

Palatability and "mouth feel" are also extremely important factors in formulating antacids. Conventional metallic carbonate and hydroxide insoluble antacid materials usually have both an unpleasant mouth feel and an unpalatable taste due to chalkiness, grittiness, dryness and astringent properties of these materials. Accordingly, the practical value of these antacid materials is substantially diminished since patients finding them objectionable may fail to take them as prescribed.

In an effort to overcome the above problems, flavorings have been employed with antacids to either mask or override the unpleasant dryness and astringent properties and chalkiness associated therewith. Unfortunately, it has been found that the flavoring merely masks the unpleasant taste, but the chalkiness, grittiness, dryness and astringent properties still remain.

It has also been suggested to coat antacid tablets with a coating material which will not dissolve in the saliva so that it masks the disagreeable taste and mouth feel and will dissolve in the stomach. However, it has been found that most coatings suggested for such use dissolve in the intestines and not the stomach and thus provide the antacid at the wrong site. Moreover, although the coating may dissolve in the stomach, the rate of dissolution may not be fast enough to allow for sufficient neutralizing reaction time of the antacid with gastric acid before the antacid is removed from the stomach by gastric emptying. U.S. Pat. No. 3,843,778 to Diamond et al. discloses a technique for coating antacid particles with a water insoluble, inert, non-toxic hydrocarbon oil which is formulated into suspensions or tablets which are said to be substantially free of the impalatable "mouth feel" properties associated with antacids. Oil coating of antacid particles cannot be carried out by mere mixing, admixing, combining, triturating or the like of an oil with antacid particles. Consequently, Diamond shows the use of an electronegative agent, such as a surfactant selected from an alkyl aryl sulfonate, or an alkyl sulfate or sulfonate, or sulfonated amides or amines, or sulfated or sulfonated esters or ethers, or a dioctyl sulfosuccinate, or a hydrated aluminum silicate, such as bentonite or kaolin, is employed to aid in adhering the oil to the electropositively charged antacid particles. The oil coating of Diamond is a monomolecular layer in very small amounts, i.e., no greater than 1:50 ratio of oil to antacid.

U.S. Pat. No. 3,253,988 to Scott discloses an orally administrable antacid formed of oils or fats, that is esters of higher fat acids and a trihydric alcohol, in combination with antacids. The Scott antacid may be in the form of a waxy solid, an emulsion or suspension.

BRIEF DESCRIPTION OF THE INVENTION

In accordance with the present invention, a non-chalky non-gritty pleasant tasting antacid tablet is provided which when exposed to saliva in the mouth disintegrates to an emulsion or colloidal suspension causing the antacid to function both systemically and organoleptically as a liquid antacid, but which is far more palatable than liquid antacids heretofore known. This phenomenon is achieved by enhancing the wettability of the individual particles of solid antacid by reducing its primary particle size, that is, predominant particle size, to less than 100 millimicrons and preferably less than 50 millimicrons, and distributing surfactant, fat or oil over such particles, while at the same time distributing flavorant, for example, chocolate, over such particles to aid the effectiveness of the fat or oil in minimizing grittiness of the antacid and enhance the textural qualities. The result is that the antacid of the invention has a pleasant non-gritty taste and provides a non-chalky smooth emulsion-like mouth feel and, because of its rapid disintegration into microscopic sized particles, allows for maximum antacid surface contact and, as a result of substantially uniform distribution of the surfactant, immediate distribution throughout the saliva and subsequently the stomach of the insoluble antacid is effected.

The non-chalky antacid tablet of the invention is comprised of antacid particles substantially homogeneously coated with a fat or oil, flavorant, a surfactant, a substrate or bulking material, which will preferably be a sweetening agent, additional favoring agent, and secondary sweeteners which are mixed with the antacid particles. The solid antacid particle size preferably has a primary particle size of less than about 100 millimicrons, and more preferably less than about 50 millimicrons.

The antacid material will be present in an amount within the range of from about 10 to about 50% by weight and preferably from about 15 to about 30% by weight. Examples of antacids suitable for use herein comprise any relatively water insoluble antacid acceptable to the Food & Drug Administration, such as, aluminum carbonate, aluminum hydroxide (or as aluminum hydroxide—hexitol stabilized polymer, aluminum hydroxide—magnesium hydroxide codried gel, aluminum hydroxide—magnesium trisilicate codried gel, aluminum hydroxide—sucrose powder hydrated), aluminum phosphate, aluminum hydroxy carbonate, dihydroxy aluminum sodium carbonate, aluminum magnesium glycinate, dihydroxy aluminum aminoacetate, dihydroxyaluminum aminoacetic acid, bismuth aluminate, bismuth carbonate, bismuth aluminate, bismuth carbonate, bismuth subcarbonate, bismuth subgallate, bismuth subnitrate, calcium carbonate, calcium phosphate, hydrated magnesium aluminate activated sulfate, magnesium aluminate, magnesium aluminosilicates, magnesium carbonate, magnesium glycinate, magnesium hydroxide, magnesium oxide and magnesium trisilicate.

Preferred antacids include aluminum hydroxide, magnesium carbonate and mixtures thereof as well as calcium carbonate and magnesium hydroxide.

The fats or oils used may be of animal, vegetable or mineral origin, which are substantially water-insoluble, inert, non-toxic hydrocarbon fats and oils and derivatives thereof, and may comprise any of the commonly commercially available fats or oils approved by the Food & Drug Administration having melting points consistent with desired mouth feeling factors, such as melting points ranging from 80° to 110° F. The fats or oils are employed in amounts within the range of from about 25% to about 45%, and preferably from about 27.5% to about 35% depending upon the properties desired in the final product. Use of such high amounts of fat would normally be expected to prevent or retard the activity of the solid antacid particles. However, when included in the composition of the invention, no such antacid deactivation occurs.

Examples of fats and/or oils suitable for use herein include hydrogenated tallow, hydrogenated vegetable oil, almond oil, coconut oil, corn oil, cottonseed oil, refined linseed oil, light liquid petrolatum, heavy liquid petrolatum, olein, olive oil, palm oil, peanut oil, persic oil, sesame oil, soybean oil or safflower oil.

Preferred oils include corn oil, light and heavy liquid petrolatum, olein, olive oil, peanut oil and soybean oil.

Any surfactant approved for use in foods by the Food & Drug Administration and having an HLB value of 8 and above, may be employed in the antacid tablets of the invention in amounts ranging from about 0.05 to about 2.5% by weight and preferably in amounts ranging from about 0.1 to about 1.3% by weight.

Examples of surfactants suitable for use herein to aid in release of the antacid ingredient include alkyl aryl sulfonate, or alkyl sulfates, or sulfonated amides or amines, or sulfated or sulfonated esters or ethers, or alkyl sulfonates, or dioctyl sulfosuccinate and the like, triglycerol monostearate, triglycerol monoshortening, octaglycerol monooleate, octaglycerol monostearate, decaglycerol decaoleate, Span 60, and Tween 60 and 80.

Preferred are the polyoxyethylene sorbitan fatty acid esters, such as the stearates, oleates, palmitates and the like, for example Tween 60 and 80, as well as octaglycerol monostearate, triglycerol monostearate and triglycerol monoshortening.

The essential ingredient for masking chalkiness, grittiness, dryness and astringent properties in the antacid acid of the invention is the natural or synthetic flavorant, examples of which include cocoa, chocolate, especially mint chocolate, butter, milk, cream, vanilla, butter fat, egg or egg white, with the chocolate being preferred. Where the above flavorant is employed in amounts within the range of from about 0.05 to about 75% and preferably from about 0.05 to about 0.8% by weight of the tablet, the flavorant, together with the fat and/or oil provides a synergistic effect in minimizing grittiness and enhancing texture and mouth feel.

In one embodiment of the present invention, a chocolate-flavored, preferably mint-chocolate flavored, antacid is provided which will contain a weight ratio of chocolate:antacid of within the range of from about 1:1 to about 6:1 and preferably from about 2:1 to about 4:1. This ratio of chocolate to antacid will provide the necessary fat content required in the composition of the invention. The chocolate flavored antacid is in the form of a smooth creamy tablet which melts below body temperature and in which the chalkiness and grittiness associated with an antacid is masked.

The antacid tablet of the invention may also include other pharmaceutically acceptable agents, such as sweetening agents, including sugars, sugar alcohols, and synthetic sweeteners, such as sorbitol, xylitol, saccharin salts, free acid form of saccharin, cyclamate salts, free cyclamic acid, dihydrochalcones, L-aspartyl-L-phenylalanine methyl ester, ace sulfame and salts thereof, as well as coloring agents, and other flavoring agents.

In addition, the antacid tablet may be sealed in a sealant, such as gum arabic or starch to prevent breakage. Furthermore, the tablet may be spray coated or otherwise coated with chocolate or other standard confections coating to prevent breakage during shipment and handling and to further decrease the chalky nature of the tablet. In addition, a confections glaze may be applied over the coating to prevent premature melting during handling.

It is preferred that in formulating the antacid tablet of the invention that the antacid material have a primary particle size of less than 100 millimicrons and more preferably less than 50 millimicrons. It is also preferred that in formulating the antacid tablet that the antacid material, fat or oil, surfactant, flavorant, and lubricant be intensively mixed until complete homogeneity is achieved. Intimate mixing of physically incompatible materials can be achieved by mulling technique, in which rubbing, kneading or smearing action of a mortar and pestle is effected, or by milling. In these operations, the surfactant, fat or oil, flavorant and lubricant will be distributed over substantially each of the particles of antacid thereby imparting increased wettability to the antacid particles as compared to the wettability achieved by merely coating small particles of antacid with oil and surfactant. Wettability depends on distribution of surfactant and hydrophilic lipophilic balance, HLB, which should be above 8 in the preferred form of the invention.

EXAMPLES OF THE INVENTION

The following Examples represent preferred embodiments of the present invention.

EXAMPLE 1

An antacid tablet comprised of calcium carbonate U.S.P. (25%) as the antacid having a chocolate coating (75%) is prepared as follows.

The calcium carbonate U.S.P. is dispersed in melted chocolate coating along with a surfactant having an HLB value of above 8. In this case Tween 80 is used. The mixture is deposited into molds, each piece weighing 2.0 grams. The resultant product yields a smooth, creamy antacid tablet which melts below body temperature. The chocolate coating is found to mask the chalkiness and grittiness normally associated with an antacid tablet while imparting good texture and mouth feel.

EXAMPLE 2

An antacid of the following formulation is prepared as described below.

| Ingredient | Parts by Weight |
|---|---|
| Calcium carbonate U.S.P. | 20.7 |
| Aluminum hydroxide F-2200 | 6.7 |
| Magnesium hydroxide U.S.P. | 4 |
| Simethicone A | 1 |
| Santone 8-1-S | 1 |
| Satina II NT (Durkee) (hydrogenated vegetable oil) | 35 |
| Sugar 10 X | 31 |
| BHA (butylated hydroxyanisole) | 0.01 |
| Peppermint oil | 0.2 |
| Lecithin | 0.4 |
| Vanilla flavor 10 X | 0.2 |

The Satina II NT (hydrogenated vegetable oil) is melted and heated under agitation. The remaining ingredients are added and the mixture is homogeneously mixed and then is deposited into molds. The so-produced product is found to make a smooth creamy antacid tablet. The mixture of hydrogenated vegetable oil and vanilla flavor present masks the chalkiness and grittiness normally associated with an antacid tablet and imparts good texture and mouth feel.

EXAMPLE 3

A deposited antacid tablet was prepared according to the following formula:

| Ingredient | Percent by Weight |
|---|---|
| Calcium Carbonate U.S.P. | 25.0 |
| Satina II NT (Durkee) (hydrogenated vegetable oil) | 35.0 |
| Sugar 10 X | 38.3 |
| Lecithin | 0.4 |
| Santone 8-1-S (Durkee) (octaglycerol monostearate) | 1.0 |
| Wintergreen Oil | 0.3 |

The Satina II NT and the emulsifier, Santone 8-1-S were melted and heated to 150° F. under agitation. At that point, the remaining powdered ingredients were added also under agitation. The fat was then allowed to cool also under agitation to approximately 120° F. At this temperature, the Lecithin and flavoring, Wintergreen Oil, were added.

The molten mixture was then deposited and allowed to cool to room temperature. The resulting product was a soft, melt away antacid tablet having excellent textural qualities and no bitterness and/or astringency.

A sample of the product resulting from the last example was subjected to the monograph test for antacid products for over-the-counter human use as set forth in 21 C.F.R. part 331 dated May 23, 1975. As a result of the improved antacid composition of the present invention, the product prepared thereby passed the monograph test thereby demonstrating its safety and effectiveness for human consumption.

EXAMPLE 4

A further example of the invention is prepared utilizing intimate contacting as set forth below:

| Ingredients | Parts by Weight |
|---|---|
| Calcium Carbonate U.S.P. | 20.7 |
| Aluminum hydroxide F-220 | 6.7 |
| Magnesium hydroxide U.S.P. | 4.0 |
| Simethicone A | 1.0 |
| Santone 8-1-S | 1.0 |
| Satina II NT (Durkee) (hydrogenated vegetable oil) | 35.0 |
| Sugar 10 X | 31.0 |
| BHA (butylated hydroxyanisole) | 0.01 |
| Peppermint oil | 0.2 |
| Lecithin | 0.4 |
| Vanilla flavor 10 X | 0.2 |

Approximately one half of the Satina II NT is melted and heated to 150° F. under agitation. The calcium carbonate, aluminum hydroxide, magnesium hydroxide, and sugar are added and mixed for a few minutes. The resulting mixture resembles a paste which is then taken and passed through a three or five roll mill. Upon exiting the mill, the mass has the appearance of flakes.

The resulting flakes are then reheated to 150° F. At this point, the remainder of the Satina II NT plus the BHA, Peppermint oil, Lecithin, and Vanilla flavor are mixed into the molten mass under agitation. The mass is then cooled slightly to 120° and deposited into molds.

The antacid tablet produced as described above when consumed provides excellent smoothness with substantially no chalkiness or grittiness. This effect is attributable to the fact that the fat-oil, and surfactant are distributed over substantially the entire surface of each antacid particle, the increased homogeneity achieved by the intimate contacting, and particle size reduction which, in turn, provides maximum solid antacid particle surface on which the surfactant effects immediate distribution of the insoluble antacid throughout the saliva. This produces an emulsion-like smoothness or creaminess in the oral cavity as well as fast relief from high acidity because of the increased surface of the antacid available for reaction with acid.

In fact, it has been found that particles of antacid when coated with fat or oil, flavorant and surfactant employing ordinary mixing techniques without intimate contacting do not disintegrate in the mouth as rapidly as do the antacid tablets of the invention. The reason for this phenomena is believed to be attributed to the synergistic effect of particle size reduction and increased homogeneity achieved by intimate contacting. Accordingly, the surfactant is available for rapid wetting with saliva.

In order the test the product prepared by use of the present composition, samples prepared along the lines of Example 1 were given to a test population of approximately 30 to 40 people. The results of the consumer testing showed that the tablet exhibited fast, melt away characteristics and complete absence of chalkiness or grittiness.

Thus, while there have been described what are presently believed to be the preferred embodiments of the invention, those skilled in the art will realize that there are further and other variations and embodiments of the present invention, and it is applicants' intention to claim all such variations and embodiments.

What is claimed is:

1. In the art of forming antacid tablets by first coating particles of antacid with a coating composition and then tableting the coated particles the improvement which comprises:

employing antacid particles having a primary particle size of less than about 100 millimicrons and a melted coating composition comprising fatty material or oil, surfactant and flavorant, selected from the group consisting of cocoa, milk, cream, egg and egg white, said fatty material or oil being present in said coating composition in an amount of from about 25 to about 45% by weight, and essentially increasing the bulk density of said antacid particles during the coating thereof with said coating composition by the step of intensively mixing said antacid particles by mulling or milling so as to provide for the removal of air between said antacid particles and for the homogeneous coating of said antacid particles with said coating composition.

2. The improvement of claim 1 wherein said fat or oil content is from about 27.5% to about 35% by weight.

3. The improvement of claim 1 wherein said coating composition further comprises other components selected from the group consisting of substrate material and lubricants.

4. The improvement of claim 1 wherein said flavorant is cocoa.

5. The improvement of claim 1 wherein said antacid material is selected from the group consisting of calcium carbonate, magnesium carbonate, magnesium hydroxide, and aluminum hydroxide, or mixtures thereof.

6. The improvement of claim 1 wherein aid antacid is selected from the group consisting of aluminum hydroxide, magnesium hydroxide, and mixtures thereof.

7. The improvement of claim 1 wherein said surfactant is present in an amount within the range of from about 0.5% to about 2.5% by weight of said coating composition.

8. The improvement of claim 1 wherein said surfactant is present in an amount of from about 0.1 to about 1.3% by weight.

9. The improvement of claim 3 wherein said substrate is selected from the group consisting of sorbitol, mannitol, xylitol, dextrose, sugar, maltose or corn syrup solids.

10. The improvement of claim 1 in which a further external coating of sealant is applied to said tablet to prevent breakage during handling.

11. The improvement of claim 1 wherein said sealant comprises gum arabic or starch and a spray-dry coating over said sealant.

* * * * *